United States Patent [19]

Scolastico et al.

[11] 4,188,484

[45] Feb. 12, 1980

[54] (2-PYRIMIDINYL-THIO)-ALKANOIC ACID AMIDES AND THEIR PREPARATION

[75] Inventors: Carlo Scolastico; Giovanni Tronconi, both of Milan, Italy

[73] Assignee: L'Instituto Farmaceutico S.p.A., Balsamo, Italy

[21] Appl. No.: 947,094

[22] Filed: Sep. 29, 1978

Related U.S. Application Data

[63] Continuation of Ser. No. 771,579, Feb. 24, 1977, abandoned.

[30] Foreign Application Priority Data

Mar. 17, 1976 [IT] Italy .................................. 21317 A/76

[51] Int. Cl.² ................. A61K 31/505; C07D 239/42; C07D 413/12; A61K 31/535

[52] U.S. Cl. .................................... 544/317; 544/122; 424/248.51; 424/251

[58] Field of Search ......................... 544/317; 424/251

[56] References Cited

U.S. PATENT DOCUMENTS 3,814,761  6/1974  Santilli .......................... 260/256.5 R

*Primary Examiner*—Alton D. Rollins
*Assistant Examiner*—Lisa Jones
*Attorney, Agent, or Firm*—Allan R. Plumley

[57] ABSTRACT

The invention provides novel amides of (2-pyrimidinyl-thio)-alkanoic acids having antilipemic activity combined with a lower toxicity than the corresponding acids.

11 Claims, No Drawings

(2-PYRIMIDINYL-THIO)-ALKANOIC ACID AMIDES AND THEIR PREPARATION

This is a continuation of application Ser. No. 771,579, filed Feb. 24, 1977, now abandoned.

The present invention relates to (2-pyrimidinyl-thio)-alkanoic acid amides and their preparation.

(2-pyrimidinyl-thio) alkanoic acids, their esters, amides and hydrazides, are described in the U.S. Pat. No. 3,814,761, and are stated to have an antilipemic effect. The substituted amides, which are the subject of the present invention, are structurally new and have a much lower toxicity, in relation to their activity, than the compounds described in the patent cited.

The amides of the present invention have the formula (I):

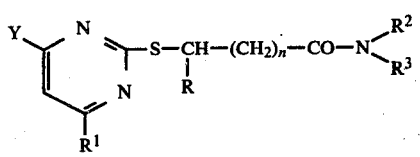 (I)

where Y is halogen; R is hydrogen or alkyl of 1 to 4 carbon atoms; $R^1$ is halogen, a radical of formula:

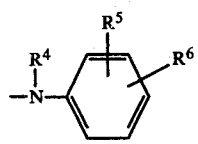

where $R^4$ is hydrogen or alkyl of 1 to 4 carbon atoms, and $R^5$ and $R^6$, which may be the same or different, are hydrogen, halogen, methyl or methoxy, a radical of formula:

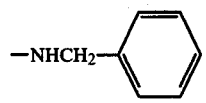

or a radical of formula:

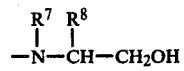

where $R^7$ and $R^8$, which may be the same or different, stand for hydrogen or alkyl of 1 to 4 carbon atoms; n is 0, 1 or 2; and $R^2$ and $R^3$, which may be the same or different, represent straight or branched alkyl or alkenyl of up to 10 carbon atoms, cycloalkyl of up to 10 carbon atoms, or straight or branched hydroxyalkyl or mercaptoalkyl of 2 to 5 carbon atoms, or $R^2$ and $R^3$ may be joined to form with the adjacent nitrogen a heterocyclic saturated 5 or 6 membered ring which may contain another hetero atom, and $R^2$ may also represent hydrogen.

Particularly preferred compounds of the invention are compounds of the formula (I) in which: Y is chlorine, R is hydrogen, $R^1$ is a

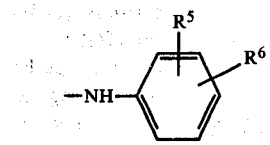

residue (where $R^5$ and $R^6$ have the aforestated meanings), or a benzylamine residue, n is 0, and $R^2$ and $R^3$, which may be the same or different, are straight or branched alkyl or alkenyl of up to 10 carbon atoms, straight or branched hydroxyalkyl or mercaptoalkyl of 2 to 5 carbon atoms, and $R^2$ may also represent hydrogen.

Examples of $R^1$ radicals of formula:

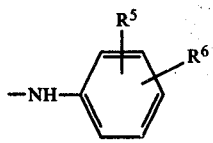

are radicals corresponding to the following amines: aniline, 2,3-xylidine, 4-chloro-aniline, 4-methoxy-aniline, 2,4,6-trimethyl-aniline, 3,4-dichloro-aniline, 4-fluoro-aniline, 3-trifluoromethyl-aniline, and 4-phenyl-aniline. Other preferred radicals of formula $-NR^2R^3$ are the benzylamine residue,

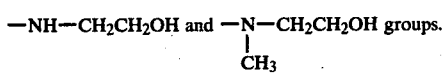

According to a feature of the invention, the compounds of formula (I) are prepared by reacting an acid derivative of the formula:

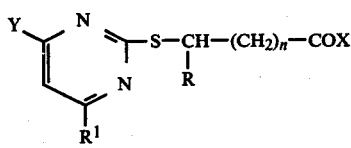 (II)

with an amine of the formula:

 (III)

where Y, R, $R^1$, $R^2$, $R^3$ and n are as defined above, and X represents halogen (preferably chlorine) or a O—CO—OC$_2$H$_5$ residue.

When X represents chlorine, the acyl chloride of formula (II) is obtained by treatment of the corresponding (2-pyrimidinyl-thio) alkanoic acid with SOCl$_2$ or oxalyl chloride in benzene solution. The compounds of formula (II) so obtained need not be isolated but may be treated directly with the amine of formula (III), when necessary in the presence of tertiary bases.

When, on the other hand, the compound of formula (II) is a mixed anhydride (X=O—VCO—OC$_2$H$_5$), it is prepared by the treatment of the corresponding (2-pyrimidinyl-thio)-alkanoic acid with ethyl chlorocarbonate in the presence of a tertiary base (preferably triethylamine), in a solvent such as tetrahydrofuran, chloroform or acetone. In this case also the compound of formula (II) need not be isolated and may be directly transformed into the final product of formula (I) by reaction with the desired amine of formula (III).

Alternatively, the compounds of formula (I) may be prepared by direct treatment of the corresponding (2-pyrimidinyl-thio)-alkanoic acid with 2 mols of an amine of formula (II), 2 mols of triethylamine and 2 mols of BF₃-etherate, in benzene or toluene solution, and refluxing, the mixture being kept in an anhydrous condition with MgSO₄, using the technique described by J. Tani, J. Dine and I. Inouf in Synthesis, 714, 1975.

In the particular case where the —NR²R³ group in the compound of formula (I) represents a β-hydroxyalkylamine residue, the preparation may be carried out by reacting the corresponding acid with an aziridine of the formula:

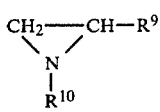

where $R^9$ and $R^{10}$ each represent hydrogen or alkyl of 1 to 3 carbon atoms and $R^{10}$ may also denote —CH₂CH₂OH.

The compounds of formula (I) in which Y denotes chlorine and $R^1$ is as defined above but is not halogen, may be obtained by treating an amide of a (4,6-dichloro-2-pyrimidinyl-thio)-alkanoic acid of formula:

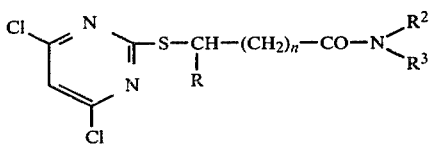    V where R,R²,R³ and n are as defined above with two equivalents of an amine of formula:

    VI where $R^1$ is as defined above but is not halogen, with fusion.

The (4,6-dichloro-2-pyrimidinyl-thio)-alkanoic acids of the formula (VII) may be prepared by acid hydrolysis of the corresponding esters (VIII), obtainable for example by the method described in U.S. Pat. No. 3,814,761, by condensation of sodium thiobarbiturate with a bromo-ester of formula (IX) and subsequent reaction with POCl₃:

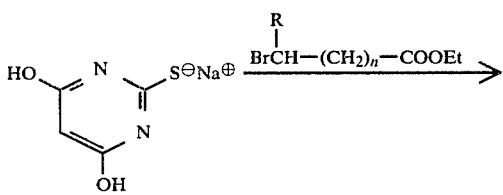

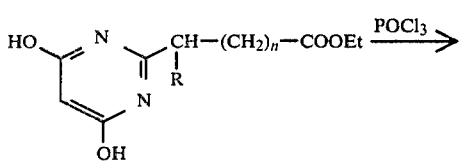

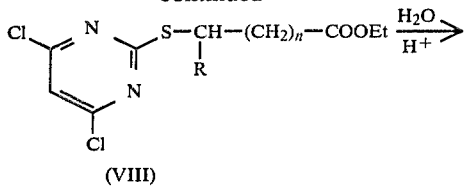 (VIII)

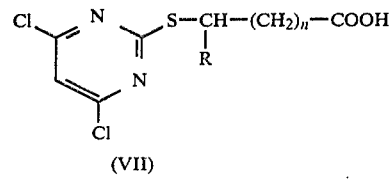 (VII)

where R and n have the aforesaid meanings and Et denotes an ethyl residue.

The compounds of the present invention are all much less toxic than the corresponding free acids. For example the [4-chloro-6-(2,3-xylidino)-2-pyrimidinyl-thio]-(N-β-hydroxyethyl)-acetamide, administered in a single dose, orally, to mice, did not cause the death of any animal, at a dosage corresponding to the LD₁₀₀ for the corresponding [4-chloro-6-(2,3-xylidino)-2-pyriminyl-thio]-acetic acid. [4-chloro-6-(2,3-xylidino)-2-pyrimidinyl-thio]-(N-β-hydroxyethyl)-acetamide at 5 g/kg/bodyweight did not cause the death of any animal among rats or mice, male or female, while the [4-chloro-6-(2,3-xylidino)-2-pyrimidinyl-thio]-acetic acid administered orally gave, for male mice, a LD₅₀ of 1155 mg/kg (9703-1374) calculated according to the method of Litchfield and Wilcoxon. In the same way, the compounds of the formula:

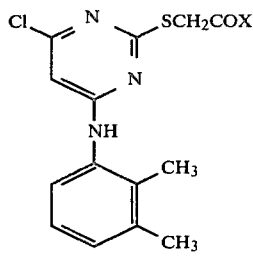

where X=—N(CH₂—CH₂OH)₂; —NH(CH₂CH₂CH₂OH); —NH(CH₂CH₂CH₂CH₂OH); —NHCH(CH₃)CH₂OH; —NH(CH₂CH₃); —NH(CH₂CH₂CH₃); —NH(CH₂CH₂CH₂CH₃); or —N(CH₂CH₃)₂ did not cause, at 5 g/kg/bodyweight, the death of any animal. Toxicological researches, medium term, show that, with equal dosage, [4-chloro-6-(2,3-xylidino)-2-pyrimidinyl-thio]-(N-β-hydroxyethyl-)acetamide is less toxic than the [4-chloro-6-(2,3-xylidino)-2-pyrimidinyl-thio]-acetic acid, particularly on the liver. The notable reduction of toxicity shown by the compounds of the present invention, particularly those containing alkyl or hydroxy-alkyl chains of up to four carbon atoms, is not accompanied by any diminution in activity compared with the relevant free acid. The compounds reduce the concentration of triglycerides and cholesterol in the blood serum of normal rats or rats treated with a hypercholesterolizing diet. In particular, with the Buchanan test (in which the pharmacological preparation is administered to normal rats for four days and analysis of the serum cholesterol is carried out on the fifth day), compounds which lower the serum cholesterol by at least 20% at a dose of 400 mg/kg are considered as active. A standard preparation, represented by Chlofibrate, at a dose of 200 mg/kg, reduces by 20% the serum cholesterol level. With this test, with varying values of X, the following results were obtained:

| X | dose:mg/kg | % reduction of serum cholesterol level |
|---|---|---|
| OH | 50 | 30.28 |
| NHCH$_2$CH$_2$OH | 56 | 30.70 |
| N(CH$_2$CH$_2$OH)$_2$ | 64 | 28.70 |
| NHCH(CH$_3$)CH$_2$OH | 59 | 31.20 |
| NH(CH$_2$)$_3$CH$_3$ | 58 | 35.00 |
| NHCH$_2$CH$_3$ | 54 | 24.20 |
| N(C$_2$H$_5$)$_2$ | 54 | 15.00 |
| NHC$_3$H$_7$ | 56 | 21.00 |
| NH(CH$_2$)$_2$CH$_2$OH | 50 | 15.00 |
| NH(CH$_2$)$_3$CH$_2$OH | 50 | 19.00 |

In the blood serum of normal rats or those on a hypercholesterol diet, treated with [4-chloro-6-(2,3-xylidino)-2-pyrimidinyl-thio]-(N-β-hydroxyethyl)-acetamide abnormal steroids, perhaps derived from the synthetic path for cholesterol, did not appear.

An appropriate dosage for the compounds of the invention is 10 to 200 mg of the active principle as a single dose. Useful pharmacutical forms are:

| Capsules: composition per 100 mg | |
|---|---|
| [4-chloro-6-(2,3-xylidino)-2-pyrimidinyl-thio]-(N-62 - hydroxyethyl)-acetamide | 50 mg |
| lactose | 49 mg |
| magnesium stearate | 1 mg |
| Tablets: composition per 100 mg | |
| [4-chloro-6-(2,3-xylidino)-2-pyrimidinyl-thio]-(N-β-hydroxyethyl)-acetamide | 50 mg |
| starch | 27 mg |
| lactose | 18 mg |
| talc | 4 mg |
| magnesium stearate | 1 mg |

The analytical data on the compounds described in the Examples are shown in Table 1 below.

EXAMPLE 1

[4-Chloro-6-(2,3-xylidino)-2-pyrimidinyl-thio]-(N-β-hydroxyethyl)-acetamide

To a suspension of [4-chloro-6-(2,3-xylidino)-2-pyrimidinyl-thio]-acetic acid (60 g.) in chloroform (1200 ml.), at ambient temperature, ethylene-imine (5.4 ml.) in chloroform (60 ml.) was added and the solution was heated to boiling for four hours. The mixture was cooled to ambient temperature, another 2.7 ml. ethylene-imine in chloroform (30 ml.) was added, and the mixture was heated for another four hours. After a final addition of 1.35 ml. ethylene-imine in chloroform (15 ml.) and a further heating to boiling for four hours, the mixture was concentrated to a small volume (300 ml.). The precipiteted solid was filtered off and recrystallised several times from acetone. 40 g. of [4-chloro-6-(2,3-xylidino)-2-pyrimidinyl-thio]-(N-β-hydroxyethyl)-acetamide were obtained, m.p. 150°–151° C.

Using the same method the following compounds were prepared:

EXAMPLE 2

[4-Chloro-6-(2,3-xylidino)-2-pyrimidinyl-thio]-(N,N-bis-β-hydroxyethyl)-acetamide m.p. 166°–167° C. (acetone).

EXAMPLE 3

[4-Chloro-6-(2,3-xylidino)-2-pyrimidinyl-thio]-N-(α-methyl-β-hydroxyethyl)-acetamide m.p. 170°–172° C. (acetone).

EXAMPLE 4

[4-Chloro-6-(p-chloroanilino)-2-pyrimidinyl-thio]-N-β-hydroxyethyl)-acetamide m.p. 145°–147° C. (ethanol/water).

EXAMPLE 5

[4-Chloro-6-benzylamino-2-pyrimidinyl-thio]-(N-β-hydroxyethyl)-acetamide m.p. 117°–119° C.; (ethanol/water).

EXAMPLE 6

[4-Chloro-6-anilin-2-pyrimidinyl-thio]-(N-β-hydroxyethyl)-acetamide m.p. 136°–138° C. (ethanol/water).

EXAMPLE 7

[4-Chloro-6-(p-methoxyanilino)-2-pyrimidinyl-thio]-(N-β-hydroxyethyl)-acetamide m.p. 119°–121° C. (ethanol/water)

EXAMPLE 8

(a)

Ethyl[4-Chloro-6-(N-methyl-N-β-hydroxyethylamino)-2-pyrimidinylthio]-acetate

A mixture of ethyl(4.6-dichloro-2-pyrimidinyl-thio)-acetate (16 g.), anhydrous sodium carbonate (3.7 g.), N-methylamino-ethanol (5.9 ml.) in ethanol (100 ml.) was heated to boiling, with agitation, for 16 hours. The mixture was filtered and water (400 ml.) added to cause precipitation. The mixture was then left for 60 minutes at 0° C. The solid precipitate was filtered off and recrystallised from ethanol/water. 13 g. of ethyl[4-Chloro-6-(N-methyl-N-β-hydroxyethylamine)-2-pyrimidinyl-thio]-acetate were obtained, m.p. 73°–74° C.

(b)

[4-Chloro-6-(N-methyl-N-β-hydroxyethylamino)-2-pyrimidinyl-thio]-acetic acid

A solution of 5.6 g. of the above-described ester in 30 ml. ethanol, with an addition of 0.7 g. NaOH in 8 ml. water, was boiled for two minutes, then diluted with 160 ml. water and extracted with ether. The aqueous phase was acidified with 17.6 ml. of HCl 1 N and evaporated to dryness. From crystallisation of the residue from about 60 ml. acetone, 4 g. of the desired acid was obtained, m.p. 188°–190° C.

(c)

[4-Chloro-6-(N-methyl-N-β-hydroxyethylamino)-2-pyrimidinyl-thio]-(N-β-hydroxyethyl)-acetamide Operating as in Example 1, by reaction of ethylene-imine with [4-chloro-6-(N-methyl-N-β-hydroxyethylamino)-2-pyrimidinyl-thio]-acetic acid, the corresponding N-β-hydroxyethyl-amide was obtained, in a good yield, m.p. 119°–121° C. (ethyl acetate).

EXAMPLE 9

[4-Chloro-6-(2,3-xylidino)-2-pyrimidinyl-thio]-(N-β-hydroxyethyl)-acetamide

To the solution of [4-chloro-6-(2,3-xylidino)-2-pyrimidinyl-thio]-acetic acid (85 g.), triethylamine (45 ml.), in anhydrous chloroform (750 ml.), cooled to −5° C., 35 ml. of ethyl chlorocarbonate and then 22 ml. of ethanolamine were added with stirring while the temperature was kept below +10° C. The reaction mixture was washed with water (350 ml.), and dried over sodium sulphate and the solvent was removed under reduced pressure. The residue was washed with benzene (500 ml.) and crystallised several times from acetone. 55 g. of [4-chloro-6-(2,3-xylidino)-2-pyrimidinyl-thio]-(N-β-hydroxyethyl)-acetamide were obtained, identical with the compound prepared as in Example 1.

Using the same method the following compounds were prepared:

EXAMPLE 10

[4-Chloro-6-(2,3-xylidino)-2-pyrimidinyl-thio]-(N-ethyl)-acetamide m.p. 191°–192° C. (acetone)

EXAMPLE 11

[4-Chloro-6-(2,3-xylidino)-2-pyrimidinyl-thio]-(N-n-propyl)-acetamide m.p. 146°–148° C. (benzene).

EXAMPLE 12

[4-Chloro-6-(2,3-xylidino)-2-pyrimidinyl-thio]-(N-i-propyl)-acetamide m.p. 156°–158° C. (benzene).

EXAMPLE 13

[4-Chloro-6-(2,3-xylidino)-2-pyrimidinyl-thio]-(N-n-butyl)-acetamide m.p. 137°–139° C. (diethyl ether).

EXAMPLE 14

[4-Chloro-6-(2,3-xylidino)-2-pyrimidinyl-thio]-(N-n-hexyl)-acetamide m.p. 116°–118° C. (benzene/hexane).

EXAMPLE 15

[4-Chloro-6-(2,3-xylidino)-2-pyrimidinyl-thio]-(N-n-octyl)-acetamide m.p. 144°–146° C. (benzene).

EXAMPLE 16

[4-Chloro-6-(2,3-xylidino)-2-pyrimidinyl-thio]-(N-allyl)-acetamide, m.p. 143°–145° C. (benzene/hexane).

EXAMPLE 17

[4-Chloro-6-(2,3-xylidino)-2-pyrimidinyl-thio]-(N-cyclohexyl)-acetamide m.p. 156°–158° C. (acetone).

EXAMPLE 18

[4-Chloro-6-(2,3-xylidino)-2-pyrimidinyl-thio]-(N,N-diethyl)-acetamide, m.p. 104°–106° C. (ethyl acetate/hexane).

EXAMPLE 19

[4-Chloro-6-(2,3-xylidino)-2-pyrimidinyl-thio]-(N-β-mercapto-ethyl)-acetamide, m.p. 117°–119° C. (ethyl acetate/hexane).

EXAMPLE 20

[4-Chloro-6-(2,3-xylidino)-2-pyrimidinyl-thio]-(N-morpholino)-acetamide m.p. 106°–108° C. (ethyl acetate/hexane).

EXAMPLE 21

[4-Chloro-6-(2,3-xylidino)-2-pyrimidinyl-thio]-(N-piperidino)-acetamide m.p. 113°–115° C. (methylene chloride/hexane).

EXAMPLE 22

[4-Chloro-6-(2,3-xylidino)-2-pyrimidinyl-thio]-(N-3-hydroxypropyl)-acetamide m.p. 122°–124° C. (ethyl acetate).

EXAMPLE 23

[4-Chloro-6-(2,3-xylidino)-2-pyrimidinyl-thio]-(N-4-hydroxybutyl)-acetamide m.p. 84°–86° C. (ethyl acetate).

Using the method described in Example 9 the compounds of Examples 2–7 were again prepared:

EXAMPLE 24

[4-Chloro-6-(2,3-xylidino)-2-pyrimidinyl-thio]-(N-N-butyl-acetamide

A mixture of [4-chloro-6-(2,3-xylidino)-2-pyrimidinyl-thio]-acetic acid (1.6 g.), triethylamine (1.4 ml.), n-butylamine (730 mg.), 47% $BF_3$-etherate (2.68 ml.) in anhydrous benzene (70 ml.) was heated to boiling for 24 hours. The solvent for the reaction was dehydrated by passing through a Soxhlet extractor containing magnesium sulphate. The reaction mixture washed with 10% NaOH, then with HCl, and finally with water to neutrality. It was dehydrated over sodium sulphate and the solvent evaporated in vacuo. The compound obtained was identical with that of Example 13.

EXAMPLE 25

(a) (4,6-Dichloro-2-pyrimidinyl-thio)-acetic acid

A solution of the ethyl ester of the (4,6-dichloro-2-pyrimidinyl-thio)-acetic acid (4 g.) in a mixture of glacial acetic acids (40 ml.) and HCl 37% (8 ml.) was heated to boiling for three hours. After cooling to 0° C., water and ice were added and the solid precipitate filtered off. This was purified by ether extraction of an aqueous solution of its sodium salt. This was then acidified, so that the acid could be filtered off again. It was then washed with water to neutrality and dried under vacuum over $P_2O_5$. On crystallisation from chloroform 2.5 g. of (4,6-dichloro-2-pyrimidinyl-thio)-acetic acid was obtained, m.p. 120°–122° C.

(b)

(4,6-Dichloro-2-pyrimidinyl-thio)-(N-β-hydroxyethyl)-acetamide

To a suspension of (4,6-dichloro-2-pyrimidinyl-thio)-acetic acid (2.390 g.) in anhydrous benzene (24 ml.), 1.27 ml. of oxalyl chloride in anhydrous benzene (6 ml.) was added at room temperature. The reaction mixture was heated, with agitation, to 40° C., for 30 minutes and held for another 10 minutes at 60° C. The solvent was evaporated under vacuum to give an oily residue, which was taken up again in anhydrous chloroform (50 ml.). The chloroform solution was added drop by drop to a solution of ethanolamine (1.1 ml.) in anhydrous chloroform (40 ml.) while the temperature was kept at about 15° C. The mixture was held at ambient temperature for 60 minutes and the separated solid was then filtered off. The filtrate was evaporated under vacuum to obtain a residue which was crystallised from ethyl acetate/hexane (1.5 g.), m.p. 95°–96° C.

Using the same method the following compounds were prepared:

EXAMPLE 26

(4,6-Dichloro-2-pyrimidinyl-thio)-(N-β-mercaptoethyl)-acetamide m.p. 88°–90° C. (ethyl acetate/hexane).

EXAMPLE 27

(4,6-Dichloro-2-pyrimidinyl-thio)-(N-butyl)-acetamide m.p. 109°–111° C. (ethyl acetate/hexane).

EXAMPLE 28

[4-Chloro-6-(2,3-xylidino)-2-pyrimidinyl-thio]-(N-β-hydroxyethyl)-acetamide

A mixture of (4,6-dichloro-2-pyrimidinyl-thio)-(N-β-hydroxyethyl)-acetamide, obtained as in Example 25, (0.490 g.) and 2,3-dimethylaniline (0.434 ml.) was heated until melted by immersion in an oil-bath (T: 110° C.) for 10 minutes. The solid residue thus obtained was cooled and crystallised from acetone, to give 0.400 g. of [4-chloro-6-(2,3-xylidino)-2-pyrimidinyl-thio]-(N-β-hydroxyethyl)-acetamide, identical with that made according to Example 1.

Using the same method the compounds of Examples 2 to 7 and 10 to 23 were also prepared:

TABLE

| Ex. No. | Formula | % C calc. | % C found | % H calc. | % H found | % N calc. | % N found |
|---|---|---|---|---|---|---|---|
| 1 | $C_{16}H_{19}ClN_4O_2S$ | 52.36 | 52.43 | 5.22 | 5.20 | 15.28 | 15.31 |
| 2 | $C_{18}H_{23}ClN_4O_3S$ | 52.59 | 52.37 | 5.64 | 5.48 | 13.64 | 13.53 |
| 3 | $C_{17}H_{21}ClN_4O_2S$ | 53.58 | 53.39 | 5.56 | 5.42 | 14.72 | 14.69 |
| 4 | $C_{14}H_{14}Cl_2N_4O_2S$ | 45.03 | 44.95 | 3.78 | 3.80 | 15.02 | 15.07 |
| 5 | $C_{15}H_{17}ClN_4O_2S$ | 51.04 | 50.87 | 4.86 | 4.97 | 15.89 | 15.75 |
| 6 | $C_{14}H_{15}ClN_4O_2S$ | 49.61 | 49.50 | 4.46 | 4.64 | 16.54 | 16.45 |
| 7 | $C_{15}H_{17}ClN_4O_3S$ | 48.82 | 48.95 | 4.65 | 4.64 | 15.20 | 15.12 |
| 8a | $C_{11}H_{16}ClN_3O_3S$ | 43.18 | 43.20 | 5.28 | 5.38 | 13.75 | 13.68 |
| 8b | $C_9H_{12}ClN_3O_3S$ | 38.90 | 39.05 | 4.36 | 4.30 | 15.14 | 15.10 |
| 8c | $C_{11}H_{17}ClN_4O_3S$ | 41.19 | 41.25 | 5.34 | 5.40 | 17.46 | 17.40 |
| 10 | $C_{16}H_{19}ClN_4OS$ | 54.75 | 54.61 | 5.46 | 5.50 | 15.98 | 15.87 |
| 11 | $C_{17}H_{21}ClN_4OS$ | 55.93 | 55.75 | 5.80 | 5.60 | 15.36 | 15.47 |
| 12 | $C_{17}H_{21}ClN_4OS$ | 55.93 | 56.06 | 5.80 | 5.96 | 15.36 | 15.24 |
| 13 | $C_{18}H_{23}ClN_4OS$ | 57.03 | 56.90 | 6.12 | 6.15 | 14.79 | 14.70 |
| 14 | $C_{20}H_{27}ClN_4OS$ | 59.00 | 59.15 | 6.69 | 6.52 | 13.77 | 13.80 |
| 15 | $C_{22}H_{31}ClN_4OS$ | 60.71 | 60.85 | 7.23 | 7.35 | 12.89 | 12.78 |
| 16 | $C_{17}H_{19}ClN_4OS$ | 56.24 | 56.35 | 5.28 | 5.25 | 15.45 | 15.47 |
| 17 | $C_{20}H_{25}ClN_4OS$ | 59.30 | 59.43 | 6.23 | 6.35 | 13.84 | 13.72 |
| 18 | $C_{18}H_{23}ClN_4OS$ | 57.03 | 57.29 | 6.12 | 6.07 | 14.79 | 14.68 |
| 19 | $C_{16}H_{19}ClN_4OS_2$ | 50.16 | 50.25 | 5.00 | 5.05 | 14.64 | 14.51 |
| 20 | $C_{18}H_{21}ClN_4O_2S$ | 55.00 | 55.05 | 5.39 | 5.48 | 14.27 | 14.13 |
| 21 | $C_{19}H_{23}ClN_4OS$ | 58.35 | 58.20 | 5.93 | 5.83 | 14.34 | 14.27 |
| 22 | $C_{17}H_{21}ClN_4O_2S$ | 53.58 | 53.48 | 5.56 | 5.45 | 14.72 | 14.70 |
| 23 | $C_{18}H_{23}ClN_4O_2S$ | 54.72 | 54.68 | 5.87 | 5.75 | 14.19 | 14.25 |
| 25a | $C_6H_4Cl_2N_2O_2S$ | 30.12 | 30.20 | 1.68 | 1.69 | 11.72 | 11.62 |
| 25b | $C_8H_9Cl_2N_3O_2S$ | 34.03 | 34.12 | 3.19 | 3.22 | 14.90 | 14.85 |
| 26 | $C_8H_9Cl_2N_3OS_2$ | 32.20 | 32.30 | 3.02 | 3.06 | 14.10 | 14.20 |
| 27 | $C_6H_{13}Cl_2N_3OS$ | 40.80 | 40.91 | 4.46 | 4.42 | 14.29 | 14.29 |

We claim:

1. A compound selected from the group consisting of
[4-chloro-6-(2,3-xylidino-2-pyrimidinyl-thio]-(N-β-hydroxyethyl)-acetamide,
[4-chloro-6-(2,3-xylidino)-2-pyrimidinyl-thio]-(N,N-bis-β-hydroxyethyl)-acetamide,
[4-chloro-6-(2,3-xylidino)-2-pyrimidinyl-thio]-N-α-methyl-β-hydroxyethyl)-acetamide,
[4-chloro-6-(p-chloroanilino)-2-pyrimidinyl-thio]-(N-β-hydroxyethyl)-acetamide,
[4-chloro-6-benzylamino-2-pyrimidinyl-thio]-(N-β-hydroxyethyl)-acetamide,
[4-chloro-6-anilino-2-pyrimidinyl-thio](N-β-hydroxyethyl)-acetamide,
[4-chloro-6-p-methoxyanilino)-2-pyrimidinyl-thio]-(N-β-hydroxyethyl-acetamide,
[4-chloro-6-(2,3-xylidino)-2-pyrimidinyl-thio]-(N-β-mercaptoethyl)-acetamide,
[4-chloro-6-(2,3-xylidino)-2-pyrimidinyl-thio]-(N-3-hydroxypropyl)-acetamide, and
[4-chloro-6-(2,3-xylidino)-2-pyrimidinyl-thio]-(N-4-hydroxybutyl)-acetamide.

2. A compound according to claim 1 which is [4-chloro-6-(2,3-xylidino-2-pyrimidinyl-thio]-(N-β-hydroxyethyl)-acetamide.

3. A compound according to claim 1 which is [4-chloro-6-(2,3-xylidino)-2-pyrimidinyl-thio]-(N,N-bis-β-hydroxyethyl)-acetamide.

4. A compound according to claim 1 which is [4-chloro-6-(2,3-xylidino)-2-pyrimidinyl-thio]-(N-α-methyl-β-hydroxyethyl)-acetamide.

5. A compound according to claim 1 which is [4-chloro-6-(p-chloroanilino)-2-pyrimidinyl-thio]-(N-β-hydroxyethyl)-acetamide.

6. A compound according to claim 1 which is [4-chloro-6-benzylamino-2-pyrimidinyl-thio]-(N-β-hydroxyethyl)-acetamide.

7. A compound according to claim 1 which is [4-chloro-6-anilino-2-pyrimidinyl-thio]-(N-β-hydroxyethyl)-acetamide.

8. A compound according to claim 1 which is [4-chloro-6-p-methoxyanilino)-2-pyrimidinyl-thio]-(N-β-hydroxyethyl-acetamide.

9. A compound according to claim 1 which is [4-chloro-6-(2,3-xylidino)-2-pyrimidinyl-thio]-(N-β-mercaptoethyl)-acetamide.

10. A compound according to claim 1 which is [4-chloro-6-(2,3-xylidino)-2-pyrimidinyl-thio]-(N-3hydroxypropyl)-acetamide.

11. A compound according to claim 1 which is [4-chloro-6-(2,3-xylidino)-2-pyrimidinyl-thio]-(N-4-hydroxybutyl)-acetamide.

* * * * *